United States Patent
Persaud et al.

(10) Patent No.: US 6,180,064 B1
(45) Date of Patent: *Jan. 30, 2001

(54) SEMICONDUCTING ORGANIC POLYMER GAS SENSOR

(75) Inventors: Krishna C. Persaud, Manchester (GB); Paolo Pelosi, Pisa (IT)

(73) Assignee: Osmetech PLC (GB)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/765,591
(22) PCT Filed: Jun. 20, 1995
(86) PCT No.: PCT/GB95/01450
 § 371 Date: Mar. 11, 1997
 § 102(e) Date: Mar. 11, 1997
(87) PCT Pub. No.: WO96/00384
 PCT Pub. Date: Jan. 4, 1996

(30) Foreign Application Priority Data

Jun. 23, 1994 (GB) .................................. 9412632

(51) Int. Cl.[7] .................................................. G01N 27/12
(52) U.S. Cl. ............................................. 422/90; 422/98
(58) Field of Search .......................... 422/98, 90, 82.01, 422/82.02; 204/291

(56) References Cited

U.S. PATENT DOCUMENTS

| 4,791,374 | 12/1988 | Yodice et al. | 324/439 |
| 4,886,625 | * 12/1989 | Albarella et al. | 204/407 |
| 5,145,645 | 9/1992 | Zakin et al. | 422/98 |
| 5,210,217 | 5/1993 | Albarella et al. | 548/527 |

FOREIGN PATENT DOCUMENTS

| 0286307 | 10/1988 | (EP) . |
| 2203553 | 10/1988 | (GB) . |
| 2221761 | 2/1990 | (GB) . |
| 2237291 | 5/1991 | (GB) . |
| 8904061 | 5/1989 | (WO) . |

OTHER PUBLICATIONS

Ferraris, J.P. et al "Poly(N–isopropyl–2, 5–di–(2–thienyl)pyrrole): a sterically hindered pyrrole–thiophene copolymer" New Polymeric Materials, vol. 2, No. 1, pp. 41–65 (1990).*

Ferraris, J.P. et al "Substitutional alloys of organic polymeric conductors" Polymer, vol. 28, No. 2, pp 179–182 (1987).*

K.C. Persaud et al, "Sensor Arrays Using Conducting Polymers for an Artificial Nose", ((Instituto di Industrie Agrarie, University of Pisa, Italy), pp. 237–257, 1992.

Julian W. Gardner et al, "A Brief History of Electronic Noses*", (Centre for Nanotechnology and Microengineering, Depto. Of Engineering, University of Warwick, Coventry, U.K.), pp. 211–220, 1994.

B.A. Gregory, "An Introduction to Electrical Instrumentation and Measurement Systems", 1982 (MacMillen).

Maisik et al., JCS Faraday Trans. 1, 1986 82, 1117–26.

* cited by examiner

*Primary Examiner*—Jeffrey Snay
(74) *Attorney, Agent, or Firm*—Christie, Parker & Hale, LLP

(57) ABSTRACT

A gas sensor comprising a pair of electrodes. The gas sensor includes one or more semiconducting organic polymers deposited between the pair of electrodes in such a manner as to effect a semiconducting electrical connection therebetween. The gas sensor also includes a device for applying an electric signal across the electrodes and a detector for detecting a chosen electrical property across the electrodes in the presence of a gas. At least one of the semiconducting organic polymers is polymerized from a monomer comprising a five membered heterocyclic aromatic ring with substituent groups at the 2 and 5 positions.

14 Claims, 3 Drawing Sheets

SEMICONDUCTING ORGANIC POLYMER GAS SENSOR

FIELD OF THE INVENTION

This invention relates to semiconducting organic polymers which may be used in gas sensors.

BACKGROUND OF THE INVENTION

It is known that certain electrochemically prepared semiconducting polymers such as polypyrrole may be employed in sensors in order to detect gases, vapors and odors. Such a sensor may comprise a pair of electrodes mounted on a substrate, with a layer of the semiconducting organic polymer deposited on and between the electrodes in order to produce an electrical connection between the electrodes. The semiconducting organic polymer may be sensitive to the presence of a gas or, more likely, to a range of gases, to the extent that adsorption of the gas onto the polymer surface affects the electrical properties of the polymer. Hence the presence of gas may be detected by monitoring, for example, the change in DC resistance of the sensor on exposure to the gas. For instance, Maisik et al (Maisik, J J, Hooper, A and Tofield, B C) JCS Faraday Trans. 1, 1986, 82, 1117–26 demonstrated a polypyrrole gas sensor displaying a DC resistance which was sensitive to the presence of nitrous oxide and hydrogen sulphide. GB-2,203,553-B discloses an improved method of detection wherein various AC impedance characteristics are measured at different AC frequencies.

A given semiconducting organic polymer will typically be sensitive to a range of compounds. Clearly this lack of selectivity is a major problem if one wishes to develop a sensor which is specific to a particular gas. Conversely, a sensor which employs a given semiconducting organic polymer may not be sufficiently sensitive to such a broad range of gases that it may be considered a general purpose device.

SUMMARY

A solution to these problems is a device which employs a plurality of sensors, wherein each sensor incorporates a different polymer and each polymer possesses differing gas response profiles. Thus a suite of polymers may be selected which possess broadly overlapping responses, but which are individually chemically tailored to enhance differences in response to certain molecules or classes of molecules. Often the variation of a substituent group on the monomer unit is sufficient to enable such "fine tuning" of response. A multi-sensor device detects gases and odors as a characteristic pattern of individual responses across the array of sensors.

The present invention relates to a class of semiconducting organic polymers based on 1, 2, 5 substituted five membered heterocyclic aromatic ring monomer units. The substituent groups at the 2 and 5 positions are preferably aromatic rings; in particular, thienyl or thienyl derivatives appear to confer enhanced stability to the resulting polymer. Further substitution at the 3 position of the ring may be desirable. By judicious variation of the substituent groups, a range of semiconducting polymers for use in gas sensors of the type described above can be produced, wherein the response profile of a polymer can be "fine tuned" to a molecule or a class of molecules.

U.S. Pat. No. 5,210,217 discloses a family of 3-substituted 2,5-di(2-thienyl)pyrrole polymers. These polymers are functionalised at the 3 position with an analyte specific receptor such as an enzyme and are employed in conductimetric liquid phase analyte detection.

According to the present invention there is provided a gas sensor which comprises:

a pair of electrodes;

one or more semiconducting organic polymers deposited onto and between the pair of electrodes in such manner as to effect a semiconducting electrical connection between said electrodes; and transduction means;

characterized in that one or more of the semiconducting organic polymers is polymerized from a monomer comprising a five membered heterocyclic aromatic ring with substituent groups at the 1, 2 and 5 positions.

The transduction means may comprise means for applying electric signal across the electrodes and detection means for detecting a chosen electrical property in the presence of a gas. For instance, if a DC electric signal is applied the change in polymer resistance on exposure of the sensor to a gas may be monitored; if an AC electric signal is applied, the change in an impedance characteristic, such as the capacitance, may be detected at a specific AC frequency.

There may be a substituent group at the 3 position.

In any of the aforementioned cases, the substituted five membered heterocyclic aromatic ring may be pyrrole.

The substituent groups at the 2 and 5 positions may be aromatic rings and, in particular, may be thienyl or derivatives thereof.

Any of the polymers described above may be polymerised electrochemically from a solution containing the monomer and a counter-ion. This counter-ion may be $BF_4^-$, $PF_6^-$, $ClO_4^-$, $C_8H_{17}SO_3^-$, $Fe(CN)_6^{3-}$ or $CH_3C_6H_4SO_3^-$.

A gas sensor in accordance with the invention will now be described with reference to the accompanying drawings.

DESCRIPTION OF THE PREFERRED EMBODIMENTS

Figure 1:
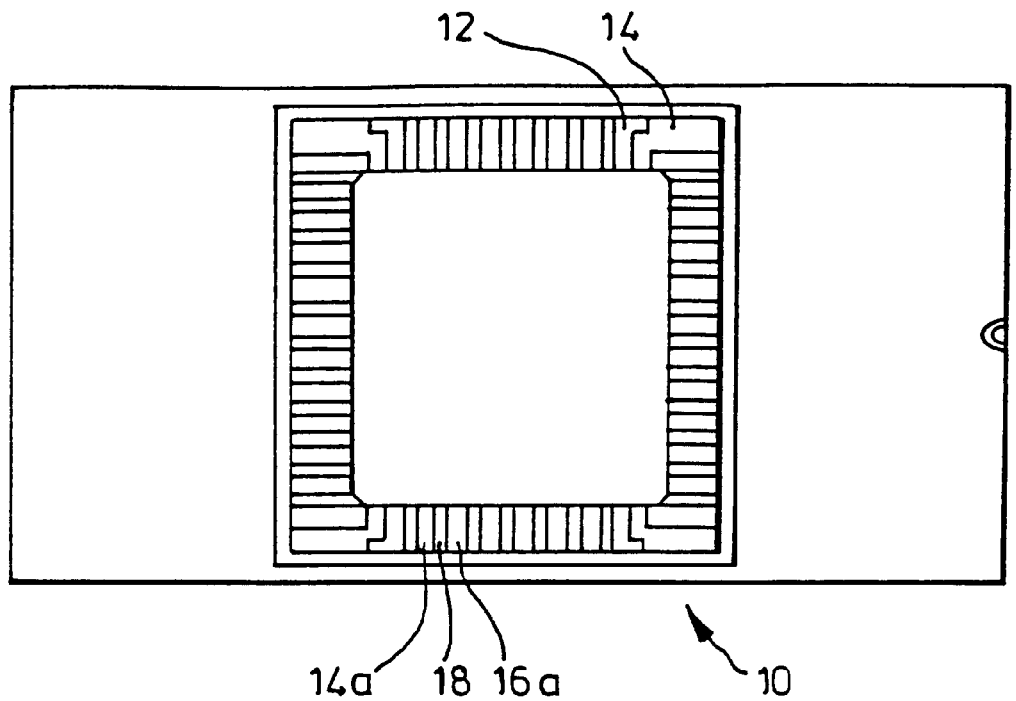
FIG. 1 shows a plan view of a silicon chip carrier.
Figure 2:
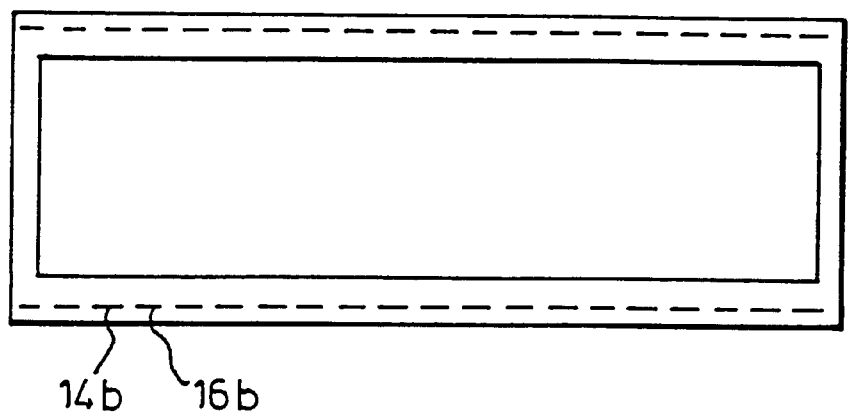
FIG. 2 shows the view from below a chip carrier.

FIGS. 1 and 2 show an embodiment of a gas sensor based on a modified 40 pin silicon chip carrier 10 (Hybritek 40 L CC), wherein the gold pins 12 of the carrier are patterned onto a ceramic substrate 14. Adjacent pins 14a and 16a act as electrodes, and a layer of a semiconducting organic polymer 18 is deposited so that there is a semiconducting electrical connection between the electrodes 14a and 16a. The electrodes are connected to plugs 14b and 16b, located on the underside of the chip carrier 10. Leads are attached to the plugs 14b and 16b in order to apply a DC potential across the electrodes 14a and 16a and the resistance of this electrical circuit is measured by known means (see, for example, B A Gregory; "An Introduction to Electrical Instrumentation and Measurement Systems", 1982, MacMillen). When the sensor is exposed to a gas to which the polymer is sensitive, the presence of the gas is detected by a variation in the DC resistance of the circuit. The semiconducting organic polymer is polymerized from a monomer which comprises a five membered aromatic heterocyclic ring, the ring having at least two substituent groups wherein one substituent group is appended at the 2 position and another substituent group is appended at the 5 position. Suitable heterocyclic rings are pyrrole, thiophene and furan.

In order to produce a polymer which displays responses to certain classes of molecules which are close to those responses desired, it is necessary to effect further substitution of the monomer at the heteroatom. The heteroatom substituent group is not limited in scope and may be, for instance, alkyl, acyl or aryl.

Similarly, it may be desirable to employ a polymer wherein the monomer is further substituted at the 3 position on the heterocyclic ring. The nature of the substituent group is not limited in scope.

A preferred choice as the five membered heterocyclic aromatic ring is pyrrole, and preferred substituents at the 2 and 5 positions are further aromatic rings. The reason for the latter preference is that the polymerization of unsubstituted pyrrole proceeds almost exclusively via linkage at the 2 and 5 positions, and therefore it is possible to inhibit polymerization if the substituents at these positions do not themselves participate in the polymerization process. The aromatic ring substituents may themselves be derivatized. A class of monomer which has proved particularly useful is N-substituted 2,5-Di(2-thienyl)-pyrrole. Polymers based on this monomer unit have proved to be particularly stable when employed in gas sensors.

Figure 3:
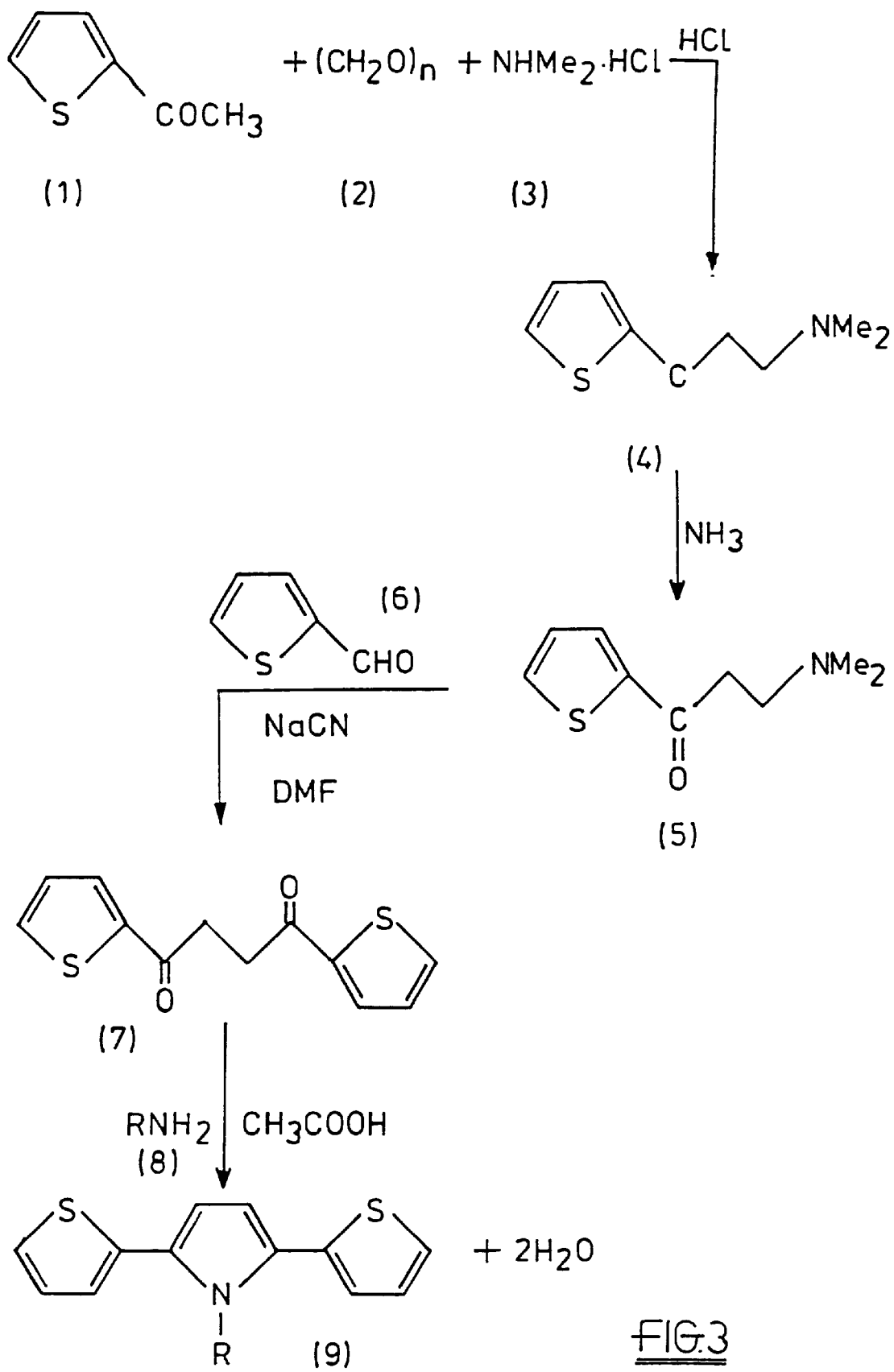
FIG. 3 shows the synthesis of N-substituted 2,5-Di-(2-thienyl)-pyrrole.

The synthesis of 2,5-Di-(2-thienyl)-pyrrole and N-substituted derivatives thereof is shown in FIG. 3. 3-dimethylamino-1-(2-thienyl)-propanone hydrochloride (4) is produced in 89% yield by refluxing for 16 hours a mixture of 2-acetylthiophene (1), paraformaldehyde (2), dimethylamine hydrochloride (3) and concentrated hydrochloric acid in ethanol. The product is isolated, treated with 35% aqueous ammonia and extracted with ether to yield 3-dimethylamino-1-(2-thienyl)-propanone (5).

A solution of 2-thiophene carboxaldehyde (6) in DMF is added under nitrogen to a suspension of sodium cyanide in DMF. The mixture is stirred and the 3-dimethylamino-1-(2-thienyl)-propanone (5) is added slowly. The mixture is allowed to stand overnight and the 1,4-Di-(2-thienyl)-1,4-butanedione product (7) is extracted with dichloromethane in 64% yield. 2,5,-Di-(2-thienyl)-pyrrole (DTP) can be produced in 80% yield by refluxing (7) for 12 hours with ammonium acetate in a mixture of acetic acid and acetic anhydride. The acid acts as a catalyst and the anhydride as a water scavenger which drives the equilibrium reaction towards the desired product. An N-substituted derivative of 2,5-DTP (9) may be produced by using an appropriate primary amine instead of ammonium acetate. The yield of (9) is often comparable to that of 2,5-DTP but does exhibit some dependence on the substituent group R; in particular, if R is bulky the yield may decrease substantially. Where appropriate, yields may be improved by the use of a benzene/acetic acid solvent system thus allowing the azeotropic removal of water from the reaction mixture by attaching a Dean-Stark trap. Alternatively, a stronger acid catalyst such as titanium (IV) chloride can be used.

Figure 4:
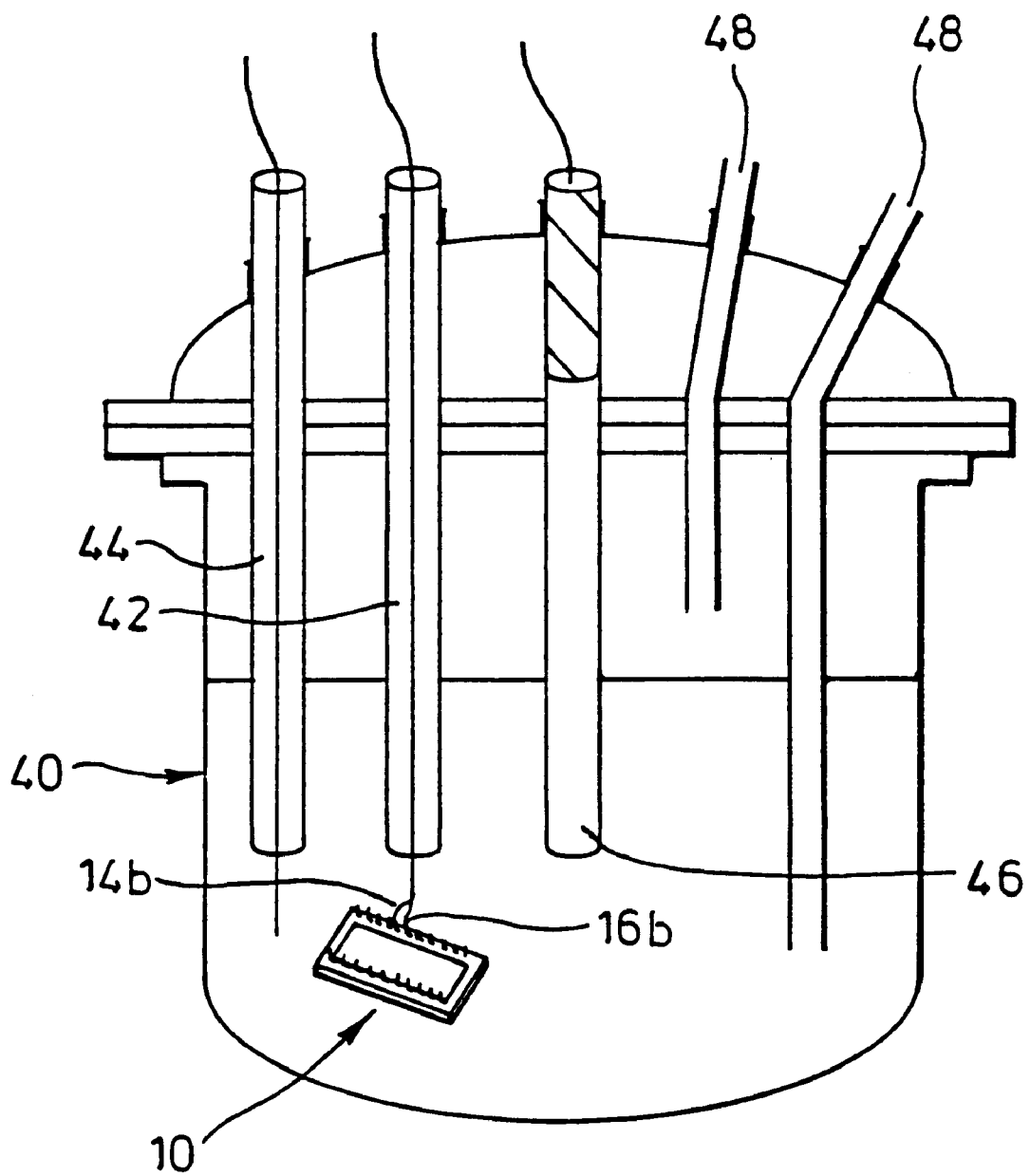
FIG. 4 shows the electrochemical polymerization process.

In order to produce the polymer in its conducting form an electrochemical polymerisation process is employed. The polymerization may be carried out by electrolytic oxidation of the monomer in an electrochemical cell. FIG. 4 shows the electrolytic oxidation of 2,5-Di-(2-thienyl)pyrrole in an electrochemical cell 40. The chip carrier 10 is connected, at plugs 14b and 16b, to the anode 42 of the cell 40. The cell 40 also comprises a cathode 44, a standard calomel reference electrode 46 and is flushed with nitrogen through ports 48. The anode 42 is at 1.3 V with respect to the reference electrode 46. The electrolyte comprises 0.01 M 2,5-Di-(2-thienyl)pyrrole and 0.1 M tetraethylammonium p-toluenesulphonate in a 99% acetonitrile/1% water medium. The further substituted variants are typically polymerized under similar conditions: the monomer concentration is typically between 0.01–0.1 M, and the solvent mixture is typically as described above, although a 50% dichloromethane, 49.5% acetonitrile, 0.5% water mixture is sometimes employed.

In solution the tetraethylammonium p-toluenesulphonate yields the tosylate anion, which is incorporated into the polymer film during polymerization as a counter-ion to ensure overall electrical neutrality in the polymer. Other counter-ions may be employed including, for example, $BF_4^-$, $PF_6^-$, $ClO_4^-$, $C_8H_{17}SO_3^-$ or $Fe(CN)_6^{3-}$. Variation of the counter-ion is another means by which the response characteristics of a polymer may be moderated.

It will be understood that the present disclosure has been made only by way of preferred embodiments and that numerous changes in details of construction, combination and configuration of the monomer and steps of processes may be resorted to without departing from the spirit and scope of the invention as herein under claimed.

What is claimed is:

1. A gas sensor which comprises:
   a pair of spaced apart electrodes;
   a layer of at least one semiconducting organic polymer deposited onto and between the pair of electrodes to effect a semiconducting electrical connection between the electrodes; and
   transduction means;
   wherein at least one of the semiconducting organic polymers is polymerized from a monomer comprising a five membered heterocyclic aromatic ring with substituent groups in only the one, two and five positions.

2. A gas sensor as recited in claim 1 wherein the transduction means comprises means for applying an electrical signal across the electrodes and detection means for detecting a chosen electrical property of the applied electrical signal in the presence of a gas.

3. A gas sensor as recited in claim 1 wherein the heterocyclic aromatic ring comprises pyrrole.

4. A gas sensor as recited in claim 1 wherein the substituent groups at the two and five positions comprise aromatic rings.

5. A gas sensor as recited in claim 4 wherein the substituent groups comprise thienyl or thienyl derivatives.

6. A gas sensor as recited in claim 1 wherein the heterocyclic aromatic ring comprises a monomer polymerized electrochemically from a solution containing the monomer and a counter-ion.

7. A gas sensor as recited in claim 6 wherein the counter-ion is selected from the group consisting of: $BF_4^-$; $PF_6^-$; $ClO_4^-$; $C_8H_{17}SO_3^-$; $Fe(CN)_6^{3-}$; and $CH_3C_6H_4SO_3^-$.

8. A gas sensor for detecting various gases, vapors and odors, the gas sensor comprising:
   a chip carrier having a ceramic substrate and at least two spaced apart electrodes;
   a layer of a semiconducting organic polymer between the spaced apart electrodes to form a semiconducting electrical connection therebetween, the polymer being polymerized from a monomer having a five membered heterocyclic aromatic ring with substituent groups at only the one, two and five positions; and
   a plurality of electrically conducting leads, each of the leads being electrically coupled to a respective electrode;
   wherein an electrical signal having an electrical characteristic is applied and measured across the electrodes to determine a change in the electrical characteristic when in the presence of a particular gas, vapor or odor.

9. A gas sensor as recited in claim 8 wherein at least one of the substituent groups is bulky and said bulky substituent is appended to the one position.

10. A gas sensor as recited in claim 8 wherein the electrical signal is an AC electrical signal and the electrical characteristic across the electrodes is the impedance at a specific AC frequency.

11. A gas sensor as recited in claim 8 wherein the substituent groups at the 2 and 5 positions are aromatic rings.

12. A silicon based chip carrier for use in a gas sensor comprising:

a chip carrier having at least two pins patterned onto a ceramic substrate, each of the pins acting as an electrode;

a layer of a semiconducting organic polymer deposited onto the chip to form a semiconducting electrical connection between the electrodes, the semiconducting organic polymer being polymerized from a monomer having a five membered heterocyclic aromatic ring with substituent groups at only the one, two and five positions; and at least two electrically conducting leads, each of the leads being electrically coupled to one of the electrodes;

wherein an electrical signal having at least one known electrical characteristic is applied across the electrodes and the known characteristic is measured to determine the presence of a particular gas, vapor or odor.

13. A silicon chip carrier for use in a gas sensor as recited in claim 12 wherein the silicon chip carrier is a modified 40 pin silicon chip carrier.

14. A silicon chip carrier for use in a gas sensor as recited in claim 12 wherein the heterocyclic ring is a monomer selected from the group consisting of: pyrrole, thiophene and furan.

* * * * *